(12) United States Patent
Schumann

(10) Patent No.: US 7,791,056 B2
(45) Date of Patent: Sep. 7, 2010

(54) GAS SENSOR FOR USE AS A FIRE DETECTOR

(75) Inventor: Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/372,301

(22) Filed: Mar. 8, 2006

(65) Prior Publication Data

US 2006/0208917 A1  Sep. 21, 2006

(30) Foreign Application Priority Data

Mar. 8, 2005  (DE) .................. 10 2005 010 454

(51) Int. Cl.
*G01N 15/06* (2006.01)
*G01N 21/49* (2006.01)
*G01N 21/85* (2006.01)

(52) U.S. Cl. .................. 250/574; 356/338; 340/630

(58) Field of Classification Search .................. 250/574; 340/630; 356/338, 339, 340, 341, 342, 343, 356/437, 442
See application file for complete search history.

(56) References Cited

U.S. PATENT DOCUMENTS

| | | | |
|---|---|---|---|
| 3,932,807 A * | 1/1976 | Wilson .................. 324/71.1 |
| 4,103,997 A | 8/1978 | Araki et al. |
| 4,415,265 A * | 11/1983 | Campillo et al. ............. 356/338 |
| 4,884,435 A * | 12/1989 | Ehara .................. 73/23.34 |
| 5,351,034 A * | 9/1994 | Berger et al. ................. 340/577 |
| 5,942,676 A * | 8/1999 | Potthast et al. ............. 73/31.06 |
| 6,084,844 A * | 7/2000 | Takeda .................... 369/112.1 |
| 7,215,414 B2 * | 5/2007 | Ross ............................ 356/71 |
| 2004/0220459 A1* | 11/2004 | Schlegel et al. ............. 600/316 |

FOREIGN PATENT DOCUMENTS

| | | |
|---|---|---|
| DE | 4445359 | 6/1996 |
| DE | 19850564 | 5/2000 |
| DE | 199 56 303 | 6/2001 |
| EP | 0926646 | 6/1999 |
| EP | 1104884 | 6/2001 |
| EP | 1379505 | 2/2007 |
| JP | 2004-037402 | * 2/2004 |

* cited by examiner

*Primary Examiner*—Thanh X Luu
*Assistant Examiner*—Francis M Legasse, Jr.
(74) *Attorney, Agent, or Firm*—Kenyon & Kenyon LLP

(57) ABSTRACT

A gas sensor includes a light source for generating light at a wavelength <550 nm, and a detector for determining a scattered radiation. The gas sensor further includes a field-effect transistor, a semiconductor diode or an ohmic resistance, which forms a unit together with the light source and/or the detector.

9 Claims, 2 Drawing Sheets

GAS SENSOR FOR USE AS A FIRE DETECTOR

FIELD OF THE INVENTION

The present invention relates to a gas sensor, and relates more particularly to a gas sensor used as a fire detector.

BACKGROUND INFORMATION

To be able to detect fires as early and reliably as possible, gas sensors are needed as fire detectors, which are able to detect fire gases in the smallest concentrations. A fire detector is described, e.g., in published German patent document DE 199 56 303, the measuring principle of which detector is based on a field-effect transistor (FET), whose gate electrode has at least one gas-sensitive coating such that the channel conductivity of the field-effect transistor changes as a function of the concentration of one or several fire gases to be detected.

The fire detector described in published German patent document DE 199 56 303 may also include, in addition to a measuring function on the basis of a FET, a scattered light detector. For this purpose, a light source is provided, which usually emits light at a wavelength in the infrared or near-infrared range into a measuring chamber, which is in contact with the surrounding atmosphere. The measuring chamber furthermore contains a detector unit, which allows for a determination of particles possibly contained in the gas phase. However, such a construction having a light source, a detector and a measuring function in the form of a FET, each as separate components, is expensive.

An object of the present invention is to provide a gas sensor which allows for a reliable and early detection of fires, but which nevertheless has a simple construction.

SUMMARY OF THE INVENTION

The gas sensor according to the present invention advantageously provides at least two of the components of the gas sensor in one unit. This allows for a fire to be detected in at least two mutually independent ways without resulting in an expensive construction of the fire detector.

It is advantageous if a scattered light detector or a light source of the gas sensor is provided on a common substrate having a field-effect transistor, a semiconductor diode or an ohmic resistance. In this manner, these components form a common and thus space-saving unit.

It is furthermore advantageous if at least one gate electrode of the field-effect transistor has a coating that is sensitive to fire gases. This coating may be manufactured on the basis of acidic or basic oxides such that it responds to the relevant basic or acidic fire gases, or on the basis of tin dioxide, resulting in a sensitivity to organic combustion products. The existence of a sensitive coating in contact with the gate electrode of the FET results in a sensitive detector for fire gases.

In an example embodiment of the present invention, the gas sensor has two light sources, which emit lights of different wavelengths, the wavelength of the light emitted by the first light source amounting to 1.1 to 3 times the wavelength of the light emitted by the second light source, for example. In this manner, it is possible to successfully detect in a very precise manner particles or aerosols having a diameter in the range of 10 to 500 nm, since based on the mutual proportion of the scattering intensities it is possible to distinguish fire-typical particles or aerosols from dust particles in the air.

DETAILED DESCRIPTION

Figure 1:
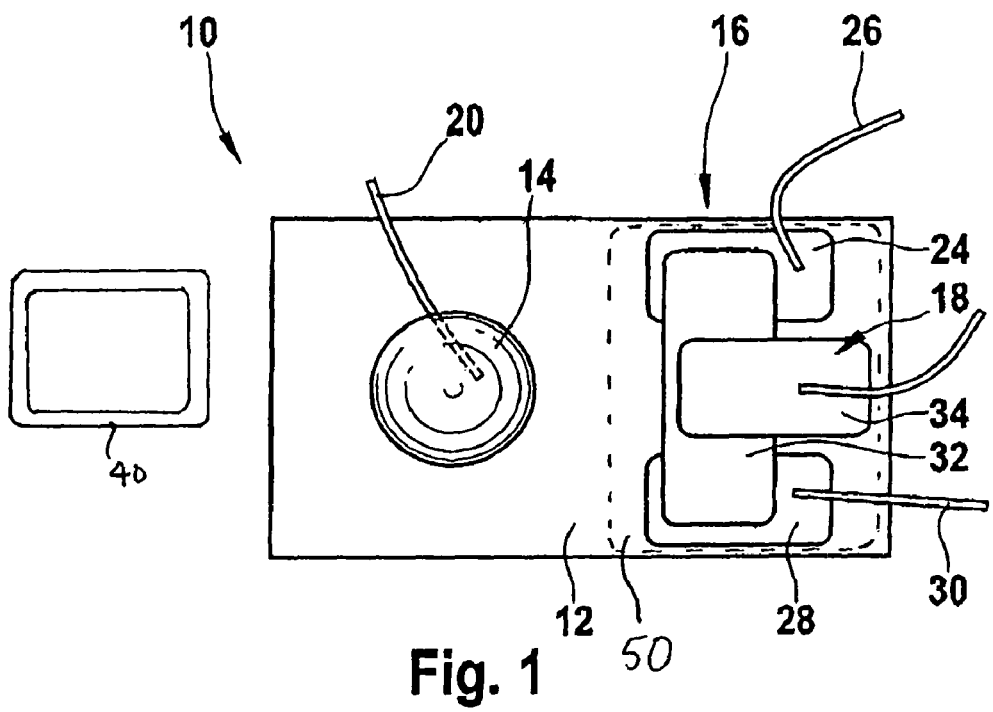
FIG. 1 shows a schematic representation of a first exemplary embodiment of a sensitive element of a gas sensor.

FIG. 1 shows a sensitive element 10 of a gas sensor, which sensitive element 10 includes a substrate 12, which in turn is produced, for example, from silicon, silicon carbide or gallium nitride, which is optionally deposited on sapphire. A light source 14 and a field-effect transistor (FET) 16 are situated on substrate 12. Additionally, a heating element 50 is optionally integrated into substrate 12, which is used to heat substrate 12 temporarily or regularly to a temperature at which substances adsorbed on the surface of the FET 16 desorb and thus a regeneration of the sensitive element 10 can be accomplished. The heating element may be configured, for example, as a meander-shaped resistor track. As an alternative or in addition to the application of a FET, a semiconductor diode or an ohmic resistance may be provided on substrate 12.

A light-emitting diode (LED), for example, is chosen as light source 14, which emits light at a wavelength of $\leq 550$ nm, e.g., in the range of 250 to 550 nm, or more particularly in the range of 350 to 550 nm. For this purpose, the LED may be manufactured on the basis of a doped semiconductor material having a band gap of 2 to approximately 5 eV. These are materials such as α- or β-gallium nitride, 6H- or β-silicon carbide, zinc oxide, α- or β-aluminum nitride, α- or β-indium nitride, zinc sulphide, zinc selenide, aluminum phosphide, gallium phosphide and aluminum arsenide, for example.

The use of an LED manufactured in this manner as light source 14 has the advantage that light of short wavelength is scattered markedly more strongly on particles in the gas phase than radiation in the NIR (near infrared) or IR (infrared) range. Another advantage of using an LED as light source 14 which provides light of short wavelength, is seen in the fact that a heating of substrate 12, on which both light source 14 as well as FET 16 or a semiconductor diode or an ohmic resistance are situated, is only possible when an LED having a great band gap is used. Other LEDs, which emit radiation in the NIR or IR range, cannot be used on heated substrates due to their increased thermally dependent conductivity. Light source 14 is electrically connected by an electrical contact 20.

FET 16 includes a source region 24, which is provided with an electrical contact 26, as well as a drain region 28, which is connected with another electrical contact 30, source region 24 and drain region 28 being mutually connected by a semiconductive, possibly doped channel region 32. A gate electrode 34 is in contact with channel region 32.

FET 16, for example, has on its gate electrode 34 a gas-sensitive coating 18, gate electrode 34 being provided with the gas-sensitive coating either partially or across its entire surface. Gas-sensitive coating 18 may be accomplished, for example, on the basis of basic oxides such as magnesium oxide, whose electrical charge distribution on the surface or in the interior changes in the presence of acidically reacting gas components such as nitrogen oxides, sulfur oxides, hydrogen halides or carbon dioxide in the surrounding atmosphere and thus results in a change of the electrical field emanating from the gate electrode.

Alternatively or additionally, gas-sensitive coating 18 may contain acidic oxides such as tantalum oxides or niobium oxides, which react particularly to the existence of basically reacting gaseous substances such as ammonia or volatile amines in the surrounding atmosphere by a change in their charge carrier distribution. Another possible option is to use semiconductors such as tin dioxide or titanium dioxide, or particles of a precious metal such as platinum, for example, or a precious metal alloy such as a platinum-gold alloy, for example, as the basis of sensitive coating 18, the use of these substances resulting in a change of the electrical charge carrier distribution in sensitive coating 18 when organic gas components such as polycondensated aromatics, hydrocarbons and carbon monoxide are absorbed. For this purpose, precious metal or precious metal alloy particles may be used in the form of nanoparticles.

As an alternative or in addition to the arrangement of a FET 16, a semiconductor diode or an ohmic resistance may also be provided on substrate 12. In this case, at least a part of the large surface exposed to a surrounding atmosphere is provided with a sensitive coating 18, sensitive coating 18 in this case being manufactured from comparable materials as were already described above as a coating for FET 16.

The gas sensor furthermore includes a detector 40 for detecting the radiation emitted by light source 14. This includes, for example, one of the doped semiconductor materials as a light-detecting material (as described above) as the base material of light source 14.

Detector 40 is positioned in such a way that it detects only a scattered radiation of the light emitted by light source 14; that is, it is in particular situated outside of the radiation cone produced by light source 14. For this purpose, detector 40 is constructed, for example, as a photodiode, a photo-sensitive resistor or as a phototransistor. Furthermore, the fire detector may contain a reflector or parabolic mirror, by which scattered light may be supplied to the detector in a bundled form.

When used as a fire detector, this construction of the gas sensor on the one hand allows for a fire to be detected by detecting scattered radiation, which is amplified particularly with the existence of soot or smoke particles or of aerosols. Moreover, a fire may be detected by determining an electrical current flowing through FET 16 or a semiconductor diode or a semiconductor resistor, the magnitude of which is dependent upon, among other things, the gases occurring in fires. This dual fire detection allows for a significantly greater system safety since both highly soot-emitting, slightly poisonous fires as well as slightly soot-emitting fires accompanied by poisonous gases are detected. Nevertheless, the total construction of the gas sensor is not expensive since at least two of components 14, 16, 40 form a unit on substrate 12 of sensitive element 10.

Figure 2:
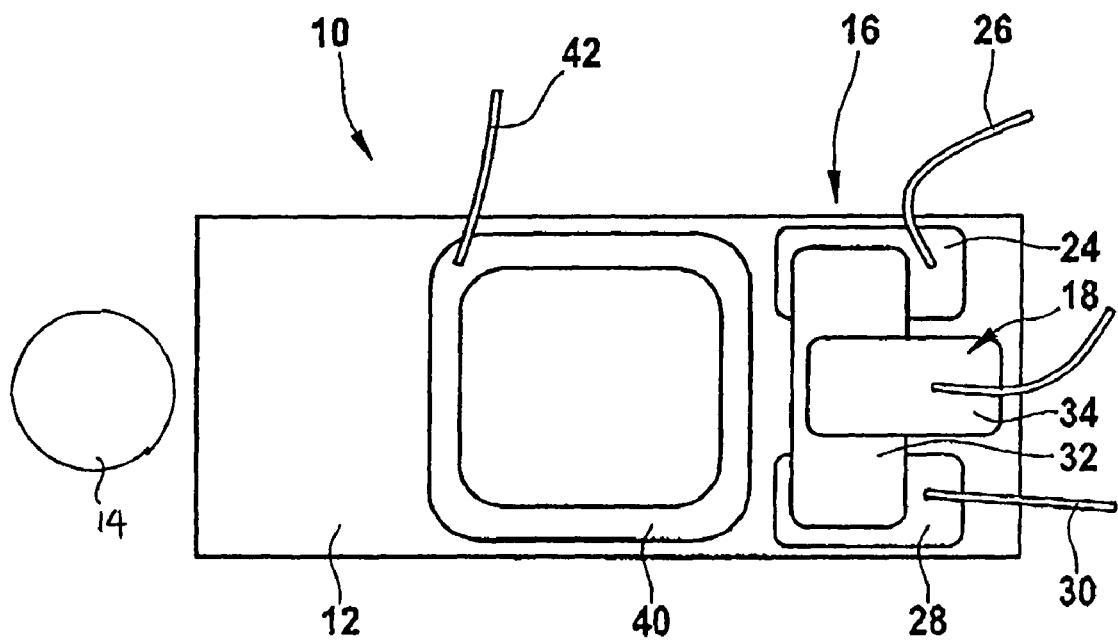
FIG. 2 shows the schematic representation of a sensitive element of a gas sensor according to a second exemplary embodiment.

Another exemplary embodiment of a sensitive elements 10 is shown in FIG. 2, identical reference numerals indicating identical components as in FIG. 1.

In this instance, instead of light source 14, a detector 40 for the radiation emitted by light source 14 is situated on substrate 12 of sensitive element 10. Detector 40 is connected by an electrical contact 42. Light source 14 in this instance is positioned separately, but in such a way that detector 40 detects only the scattered portion of the light emitted by light source 14.

Sensitive element 10 is configured in such a way that gate electrode 34 and the light-sensitive region of detector 40 are manufactured on the basis of the same semiconductor material since this substantially simplifies the manufacture of sensitive element 10. For this purpose, gallium nitride, indium-gallium nitride, aluminum-gallium nitride or silicon carbide, for example, are used as the material of detector 40.

Figure 3:
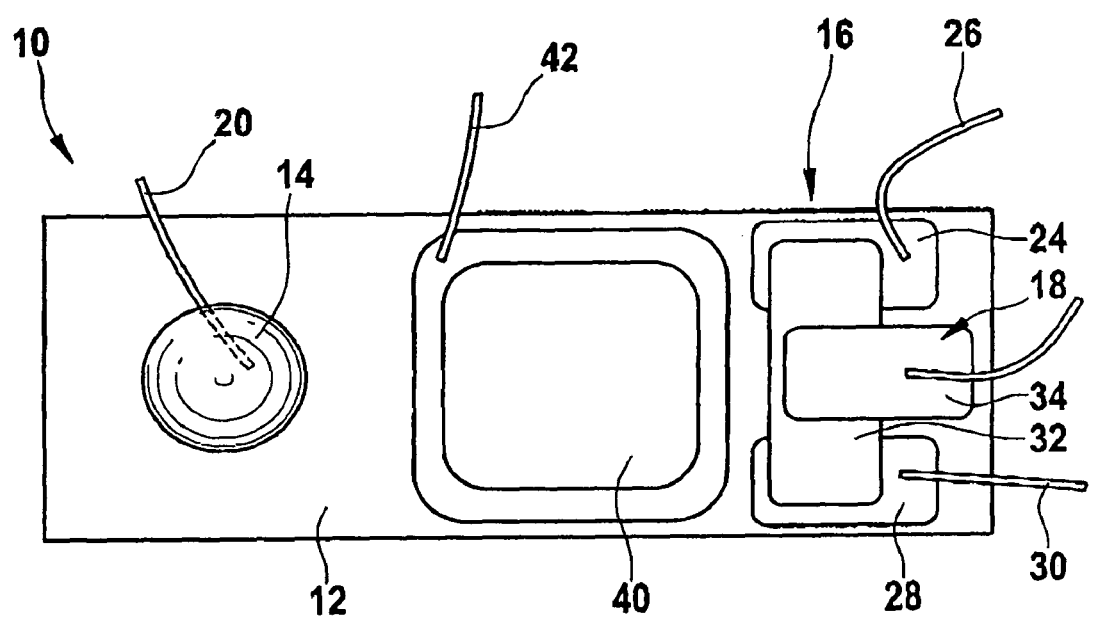
FIG. 3 shows the schematic representation of a sensitive element of a gas sensor according to a third exemplary embodiment.

Another exemplary embodiment of a sensitive elements 10 is shown in FIG. 3, identical reference numerals again indicating identical components as in FIGS. 1 and 2.

As can be gathered from FIG. 3, substrate 12 of sensitive element 10, according to the third exemplary embodiment, has in addition to FET 16 both a light source 14 as well as a detector 40. The special advantage of this setup lies in the fact that all components of the gas sensor are situated on a common substrate 12 of sensitive element 10 and that the gas sensor itself may be constructed in a cost-effective and space-saving manner.

As an alternative embodiment of the sensitive elements shown in FIGS. 1 through 3, it is possible to provide two light sources 14, which generate radiations of different wavelengths. For this purpose, it is particularly advantageous if the additional light source generates a radiation having a wavelength that corresponds to 1.1 to 3 times, e.g., 1.1 to 1.5 times, the wavelength of the radiation generated by first light source 14.

For this purpose, detector 40 detects two scattered light signals, having different light intensities, at the same time or at different times, depending on the control system of the light sources. Theoretically, the measured light intensity is a function of the wavelength of the scattered radiation according to the formula:

$$I=1/\lambda^4.$$

Consequently, intensity differences having a factor of 1.5 to 5 are to be expected between the two signals depending on the chosen wavelength of the two light sources. In this manner it is possible to detect the scattered portion of the detected light in a very precise manner, particularly the portion attributable to particles or aerosols having a particle size of 10-500 nm, as typically occur in fires.

In addition to a use as fire detector, the gas sensor according to the present invention is suitable for early detection of smoldering fires or cable fires, and as a sensor for determining gas components in exhaust gases of internal combustion engines, power plants, etc., or as air quality sensors. Furthermore, it is possible to detect harmful exhaust gas components in the exhaust gases of waste incinerators.

What is claimed is:

1. A gas sensor for use as a fire detector, comprising:
   a light source for generating light at a wavelength <550 nm;
   a detector for determining a scattered radiation;
   at least one of a field-effect transistor, a semiconductor diode and an ohmic resistor that forms, together with at least one of the light source and the detector, a single unit; and
   a semiconductor substrate, wherein the at least one of the field effect transistor, the semiconductor diode and the ohmic resistor is situated on the substrate, wherein at least one of the light source and the detector is situated on the substrate, and wherein a magnitude of a current flowing through the at least one of the field-effect transistor, the semiconductor diode, and the ohmic resistor depends upon the presence of gases occurring in fires.

2. The gas sensor as recited in claim 1, wherein at least one of a gate electrode of the field-effect transistor, a surface region of the semiconductor diode, and a surface region of the ohmic resistor has a coating that is sensitive to gases occurring in fires.

3. The gas sensor as recited in claim 2, wherein the coating contains an oxide of one of tantalum, niobium and alkaline-earth metals.

4. The gas sensor as recited in claim 2, wherein the coating contains tin dioxide.

5. The gas sensor as recited in claim 2, wherein the coating contains a precious metal alloy.

6. The gas sensor as recited in claim 2, further comprising: an additional light source, wherein the two light sources emit lights of different wavelengths.

7. The gas sensor as recited in claim 2, further comprising: a heating element.

8. The gas sensor as recited in claim 6, wherein the wavelength of light emitted by one light source is 1.1 to 3 times the wavelength of light emitted by the other light source.

9. A gas sensor for use as a fire detector, comprising:
a light source for generating light at a wavelength <550 nm;
a detector for determining a scattered radiation;
at least one of a field-effect transistor and a semiconductor diode that forms, together with at least one of the light source and the detector, a single unit,
wherein a magnitude of a current flowing through the at least one of the field-effect transistor and the semiconductor diode depends upon the presence of gases occurring in fires.

* * * * *